US012600653B2

(12) United States Patent
Hu et al.

(10) Patent No.: US 12,600,653 B2
(45) Date of Patent: Apr. 14, 2026

(54) DEVICE AND METHOD FOR COOPERATIVELY TREATING AQUACULTURE TAIL WATER

(71) Applicant: NANCHANG UNIVERSITY, Nanchang (CN)

(72) Inventors: Beijuan Hu, Nanchang (CN); Xinxin Lai, Nanchang (CN); Guilan Yu, Nanchang (CN); Yijiang Hong, Nanchang (CN)

(73) Assignee: NANCHANG UNIVERSITY, Nanchang (CN)

( * ) Notice: Subject to any disclaimer, the term of this patent is extended or adjusted under 35 U.S.C. 154(b) by 430 days.

(21) Appl. No.: 18/342,664

(22) Filed: Jun. 27, 2023

(65) Prior Publication Data

US 2024/0124339 A1 Apr. 18, 2024

Related U.S. Application Data

(63) Continuation of application No. PCT/CN2023/080986, filed on Mar. 13, 2023.

(30) Foreign Application Priority Data

Oct. 13, 2022 (CN) .......................... 202211254594.X

(51) Int. Cl.
*C02F 3/32* (2023.01)
*A01K 63/04* (2006.01)
(Continued)

(52) U.S. Cl.
CPC .............. *C02F 3/325* (2013.01); *A01K 63/04* (2013.01); *C02F 3/322* (2013.01); *C02F 3/34* (2013.01);
(Continued)

(58) Field of Classification Search
CPC .. C02F 3/325; C02F 3/322; C02F 3/34; C02F 1/001; C02F 1/004; C02F 3/102;
(Continued)

(56) References Cited

U.S. PATENT DOCUMENTS

2015/0264897 A1* 9/2015 Limcaco ................ A01K 61/00
119/224

FOREIGN PATENT DOCUMENTS

AU 2019208276 B1 1/2021
CN 107751085 A * 3/2018 ........... A01K 63/042
(Continued)

OTHER PUBLICATIONS

Machine-generated English translation of CN 107751085, generated on Oct. 22, 2025.*
(Continued)

*Primary Examiner* — Fred Prince
(74) *Attorney, Agent, or Firm* — Cooper Legal Group, LLC

(57) ABSTRACT

A device for cooperatively treating aquaculture tail water by algae and bacteria is provided, including an aquaculture part; the aquaculture part is communicated with a sewage discharge part, and the sewage discharge part is communicated with a tail water treatment part, and the tail water treatment part is communicated with the aquaculture part; the sewage discharge part includes a sewage pipe communicated with the aquaculture part, where one end of the sewage pipe away from the aquaculture part is communicated with the tail water treatment part, and a sewage pump is arranged on the sewage pipe; the tail water treatment part includes a second shell, a bottom end of the second shell is communicated with the sewage pipe, a top end of a side wall of the second shell is communicated with the aquaculture part, several guide plates are arranged in the second shell.

9 Claims, 6 Drawing Sheets

(51) Int. Cl.

| | |
|---|---|
| *C02F 1/00* | (2023.01) |
| *C02F 1/12* | (2023.01) |
| *C02F 3/10* | (2023.01) |
| *C02F 3/34* | (2023.01) |
| *C12M 1/00* | (2006.01) |
| *C12M 1/32* | (2006.01) |
| *C12N 1/12* | (2026.01) |
| *C02F 103/20* | (2006.01) |
| *C12R 1/89* | (2006.01) |

(52) U.S. Cl.
CPC ............ *C12M 21/02* (2013.01); *C12M 23/12* (2013.01); *C12M 29/06* (2013.01); *C12N 1/12* (2013.01); *C02F 1/001* (2013.01); *C02F 1/004* (2013.01); *C02F 3/102* (2013.01); *C02F 2103/20* (2013.01); *C02F 2201/009* (2013.01); *C02F 2201/46165* (2013.01); *C02F 2209/005* (2013.01); *C02F 2209/02* (2013.01); *C02F 2209/11* (2013.01); *C02F 2209/14* (2013.01); *C02F 2209/22* (2013.01); *C02F 2209/42* (2013.01); *C02F 2301/046* (2013.01); *C12R 2001/89* (2021.05)

(58) Field of Classification Search
CPC ............ C02F 2103/20; C02F 2201/009; C02F 2201/46165; C02F 2209/005; C02F 2209/02; C02F 2209/11; C02F 2209/14; C02F 2209/22; C02F 2209/42; C02F 2301/046; A01K 63/04; C12M 21/02; C12M 23/12; C12M 29/06; C12N 1/12; C12R 2001/89

USPC ............ 210/602, 614, 615, 167.22; 119/227
See application file for complete search history.

(56) References Cited

FOREIGN PATENT DOCUMENTS

| | | | | | |
|---|---|---|---|---|---|
| CN | 110188705 | A | | 8/2019 | |
| CN | 110929603 | A | | 3/2020 | |
| CN | 111242180 | A | | 6/2020 | |
| CN | 111444760 | A | | 7/2020 | |
| CN | 111626328 | A | | 9/2020 | |
| CN | 111914797 | A | | 11/2020 | |
| CN | 113537138 | A | | 10/2021 | |
| CN | 214829729 | U | | 11/2021 | |
| CN | 114716110 | A | * | 7/2022 | ............... C02F 9/00 |
| CN | 114988653 | A | | 9/2022 | |
| CN | 115124149 | A | * | 9/2022 | ............... C02F 3/32 |
| CN | 115477448 | A | | 12/2022 | |
| WO | 2020247545 | A1 | | 12/2020 | |
| WO | 2024/077858 | A1 | | 4/2024 | |

OTHER PUBLICATIONS

Machine-generated English translation of CN 114716110, generated on Oct. 22, 2025.*
Machine-generated English translation of CN 214829729, generated on Oct. 22, 2025.*
Machine-generated English translation of CN 115124149, generated on Oct. 22, 2025.*
Dang, et al. "Depth-Wise Separable Convolution Neural Network with Residual Connection for Hyperspectral Image Classification" Remote Sens. 2020, 12, 3408.

* cited by examiner

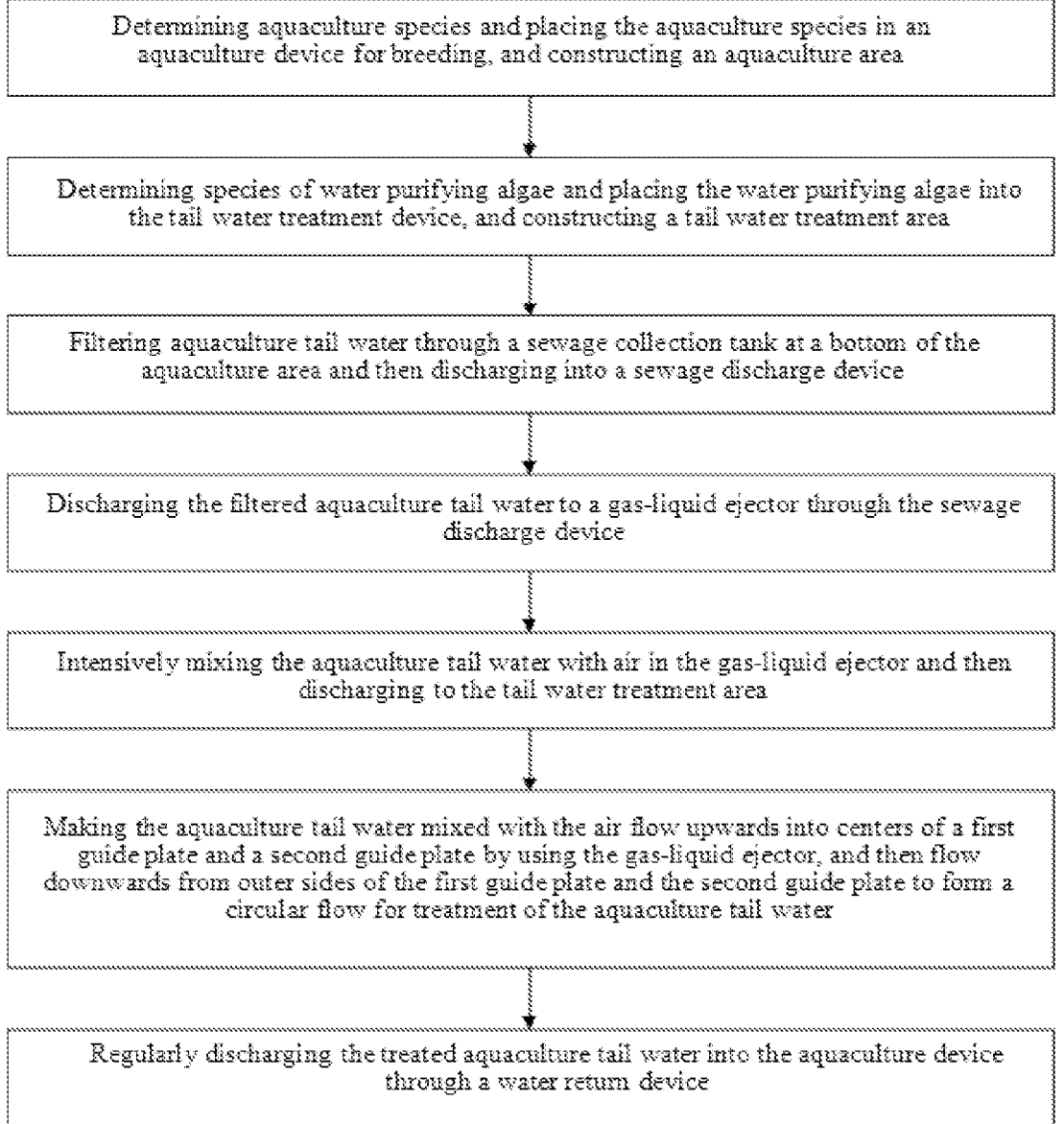

Determining aquaculture species and placing the aquaculture species in an aquaculture device for breeding, and constructing an aquaculture area Determining species of water purifying algae and placing the water purifying algae into the tail water treatment device, and constructing a tail water treatment area Filtering aquaculture tail water through a sewage collection tank at a bottom of the aquaculture area and then discharging into a sewage discharge device Discharging the filtered aquaculture tail water to a gas-liquid ejector through the sewage discharge device Intensively mixing the aquaculture tail water with air in the gas-liquid ejector and then discharging to the tail water treatment area Making the aquaculture tail water mixed with the air flow upwards into centers of a first guide plate and a second guide plate by using the gas-liquid ejector, and then flow downwards from outer sides of the first guide plate and the second guide plate to form a circular flow for treatment of the aquaculture tail water Regularly discharging the treated aquaculture tail water into the aquaculture device through a water return device

FIG. 4

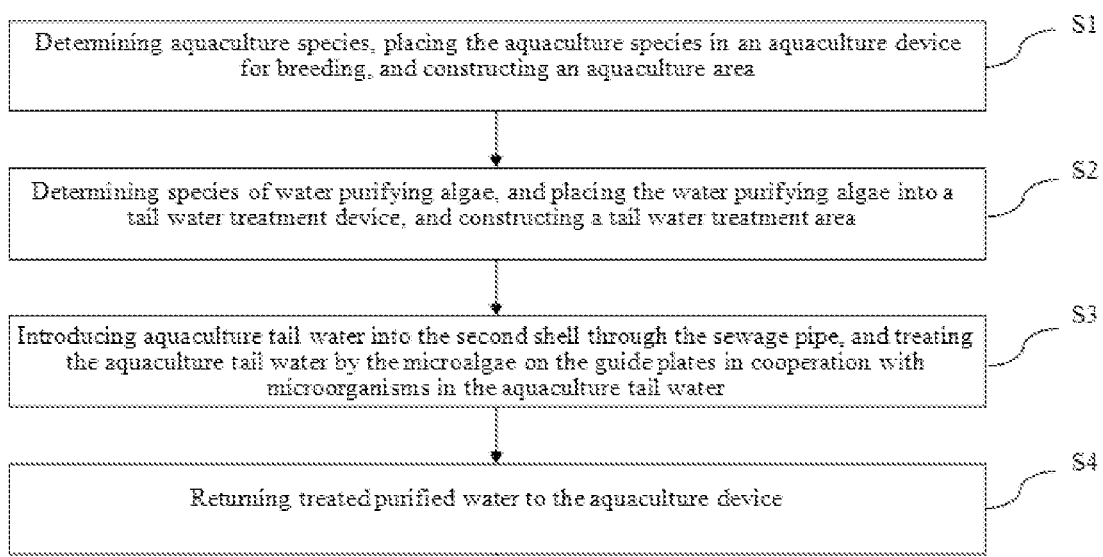

Determining aquaculture species, placing the aquaculture species in an aquaculture device for breeding, and constructing an aquaculture area ⟋ S1

Determining species of water purifying algae, and placing the water purifying algae into a tail water treatment device, and constructing a tail water treatment area ⟋ S2

Introducing aquaculture tail water into the second shell through the sewage pipe, and treating the aquaculture tail water by the microalgae on the guide plates in cooperation with microorganisms in the aquaculture tail water ⟋ S3

Returning treated purified water to the aquaculture device ⟋ S4

FIG. 6

DEVICE AND METHOD FOR COOPERATIVELY TREATING AQUACULTURE TAIL WATER

CROSS-REFERENCE TO RELATED APPLICATIONS

This disclosure is a continuation of PCT/CN 2023/080986, filed on Mar. 13, 2023, and claims priority to Chinese Patent Application No. 202211254594.X, filed on Oct. 13, 2022, the contents of which are hereby incorporated by reference.

TECHNICAL FIELD

The disclosure relates to the technical field of aquaculture tail water treatment, and in particular to a device and a method for cooperatively treating aquaculture tail water by algae and bacteria.

BACKGROUND

During or after aquaculture, tail water discharged from aquaculture systems (including aquaculture ponds, nursery ponds, factory workshops, etc.) often contains a lot of elements such as carbon, nitrogen and phosphorus, leading to eutrophication of water bodies and even soil, polluting a natural environment, and affecting production and daily life. Similar to treatment of other types of wastewater, treatment methods of aquaculture tail water may be roughly classified into three categories: physical, chemical and biological ways. General methods include flocculation, sedimentation, filtration or adsorption, etc. In practice, rich nutrients are transformed or absorbed through a combination of different methods. With enhancement of intensive and industrialized aquaculture, an aquaculture density and a feeding amount have greatly increased. How to solve pollution of residual bait feces has become a key problem in treatment of the aquaculture tail water.

Conventional technologies include filtering ponds, sedimentation ponds, constructed wetlands, algae ponds, ecological ditches, etc. These technologies have some shortcomings, such as inefficient treatment, high costs of manpower and material resources, etc. For example, an ecological treatment of aquaculture tail water in ponds by using a process of "three ponds and two dams" has gone through six steps: ecological ditch→sedimentation pond-→filter dam→aeration pond→filter dam→ecological purification pond. The steps are cumbersome and need a large occupancy area. In addition, some new technologies also have shortcomings, such as the difficulty in recovering catalyst by photocatalytic oxidation and a low utilization rate of light energy. A denitrification effect of charged microbial trickling filter is still not ideal.

It is worth noting that microalgae not only serve as raw materials for biomass energy production, but also show excellent characteristics in water purification. By constructing algae-bacteria symbionts, complementary may be formed for synergistic water purification and a water purification efficiency may be improved. Oxygen released by algae through photosynthesis is supplied to aerobic heterotrophic microorganisms for metabolic activities, while oxidative decomposition of organic pollutants is carried out by aerobic microorganisms, and metabolic products of carbon dioxide, inorganic nitrogen and phosphorus compounds are supplied to the algae as carbon sources and nutrients required by the photosynthesis. This cycle forms an interactive relationship between the bacteria and the algae. Therefore, a device and a method for cooperatively treating aquaculture tail water by algae and bacteria are provided.

SUMMARY

An objective of the disclosure is to provide a device and a method for cooperatively treating aquaculture tail water by algae and bacteria, so as to solve above problems.

In order to achieve the above objective, the disclosure provides a following scheme.

A device for cooperatively treating aquaculture tail water by algae and bacteria cooperatively includes an aquaculture part, where a bottom of the aquaculture part is communicated with one end of a sewage discharge part, and an other end of the sewage discharge part is communicated with a bottom of a tail water treatment part, and an upper side wall of the tail water treatment part is communicated with an upper side wall of the aquaculture part.

The sewage discharge part includes a sewage pipe communicated with the bottom of the aquaculture part, one end of the sewage pipe away from the aquaculture part is communicated with the bottom of the tail water treatment part, and a sewage pump is arranged on the sewage pipe.

The tail water treatment part includes a second shell, where a bottom end of the second shell is communicated with the sewage pipe, and a top end of a side wall of the second shell is communicated with the upper side wall of the aquaculture part. Several guide plates are arranged in the second shell, and microalgae are inoculated on outer side walls of the guide plates.

Optionally, the aquaculture part includes a first shell, where a first liquid level controller is arranged in the first shell, a first sensor assembly is fixedly installed on an inner side wall of the first shell, and a bottom end of the first shell is communicated with at least one sewage collection tank, and a bottom end of the sewage collection tank is communicated with the sewage pipe.

Optionally, an ecological bed substrate layer and an escape prevention net are sequentially arranged in the sewage collection tank from top to bottom. The escape prevention net is fixedly connected to an inner side wall of the sewage collection tank and horizontally arranged, and the ecological bed substrate layer is placed above the escape prevention net.

Optionally, the several guide plates are fixedly connected to an inner side wall of the second shell. The several guide plates are arranged in parallel with each other, and the guide plates are arranged vertically, and side walls of the guide plates are not in contact with the inner side wall of the second shell.

Optionally, a plurality of light-emitting strips are fixedly connected to the outer side walls of the guide plates. The plurality of light-emitting strips are sequentially arranged at intervals, and the light-emitting strips are vertically arranged. A plurality of holes are arranged between each two adjacent light-emitting strips, and the holes are arranged on each of the guide plates and penetrate through each of the guide plates, and the plurality of holes are sequentially arranged at intervals from top to bottom. Several membranes are laid on the outer wall of each of the guide plates, and each of the membranes is located between each two adjacent light-emitting strips. The membranes do not cover the holes.

Optionally, a second liquid level controller is arranged in the second shell, a second sensor assembly is fixedly installed on the inner side wall of the second shell, a flowmeter is fixedly installed on the inner side wall of the second shell, and a return pipe is fixedly connected and communicated with the side wall of the second shell. The return pipe is positioned at a top end of the second shell, and one end of the return pipe away from the second shell extends into the first shell. The return pipe is provided with a return valve, one end of the return pipe extending into the first shell is located above the first liquid level controller, an other end of the return pipe is located below the second liquid level controller, and the flowmeter is close to the other end of the return pipe.

Optionally, an outer side wall of the second shell is fixedly connected with and communicated with a sludge discharge pipe. The sludge discharge pipe is located at the bottom end of the second shell, and the sludge discharge pipe is provided with a sludge discharge valve.

Optionally, the top end of the second shell is detachably connected with a top screw cover, and the top screw cover is fixedly connected with and communicated with an exhaust valve.

Optionally, a gas-liquid ejector is arranged below the second shell, and the gas-liquid ejector is communicated with the sewage pipe and located between the sewage pump and the second shell.

A method for cooperatively treating aquaculture tail water by algae and bacteria includes following steps:

S1, determining aquaculture species, placing the aquaculture species in an aquaculture device for breeding, and constructing an aquaculture area;

S2, determining species of water purifying algae, and placing the water purifying algae into a tail water treatment device, and constructing a tail water treatment area;

S3, introducing the aquaculture tail water into the second shell through the sewage pipe, and treating the aquaculture tail water by the microalgae on the guide plates in cooperation with microorganisms in the aquaculture tail water; and S4, returning treated purified water to the aquaculture device.

The disclosure has following technical effects.

According to the disclosure, aquaculture organisms are cultured in the aquaculture part. The aquaculture tail water in the aquaculture part is sent into the second shell by the sewage pump through the sewage pipe, and the guide plates in the second shell are inoculated with the microalgae. The microalgae and original microorganisms in the aquaculture tail water form an algae-bacteria symbiont, so simultaneous carbon and nitrogen reduction and phosphorus removal, low impact on the aquaculture organisms, and significant improvement in an effluent quality without subsequent sedimentation devices may be realized. A circulating flow of water quality is promoted by the sewage pump, and fluidity and stability of an algae-bacteria reaction solution are improved by using the guide plates, thus realizing quality improvement and efficiency improvement in treating the aquaculture tail water. Moreover, a co-culture of fish, algae and bacteria is realized by coupling aquaculture and microalgae culture and recycling the aquaculture tail water. Not only are there catches, the microalgae may also be recycled and utilized, adding an economic benefit and achieving resource utilization of sewage.

BRIEF DESCRIPTION OF THE DRAWINGS

In order to provide a clearer explanation of embodiments of the disclosure or technical schemes in the prior art clearer, drawings needed in the embodiments are briefly introduced below. Obviously, the drawings described below are only some embodiments of the disclosure, and other drawings may be obtained according to these drawings without a creative work for ordinary people in the field.

FIG. 4 is a schematic flow chart of a method for cooperatively treating aquaculture tail water by algae and bacteria.

FIG. 6 is a flow chart of a method for cooperatively treating aquaculture tail water by algae and bacteria.

DETAILED DESCRIPTION OF THE EMBODIMENTS

Technical schemes in embodiments of the disclosure are clearly and completely described in the following with reference to attached drawings. Obviously, the described embodiments are only a part of the embodiments of the disclosure, but not whole embodiments. Based on the embodiments in the disclosure, all other embodiments obtained by ordinary technicians in the field without a creative labor belong to a scope of protection of the disclosure.

In order to make above objects, features and advantages of the disclosure more obvious and easier to understand, the disclosure is further described in detail with the attached drawings and specific embodiments.

Figure 1:
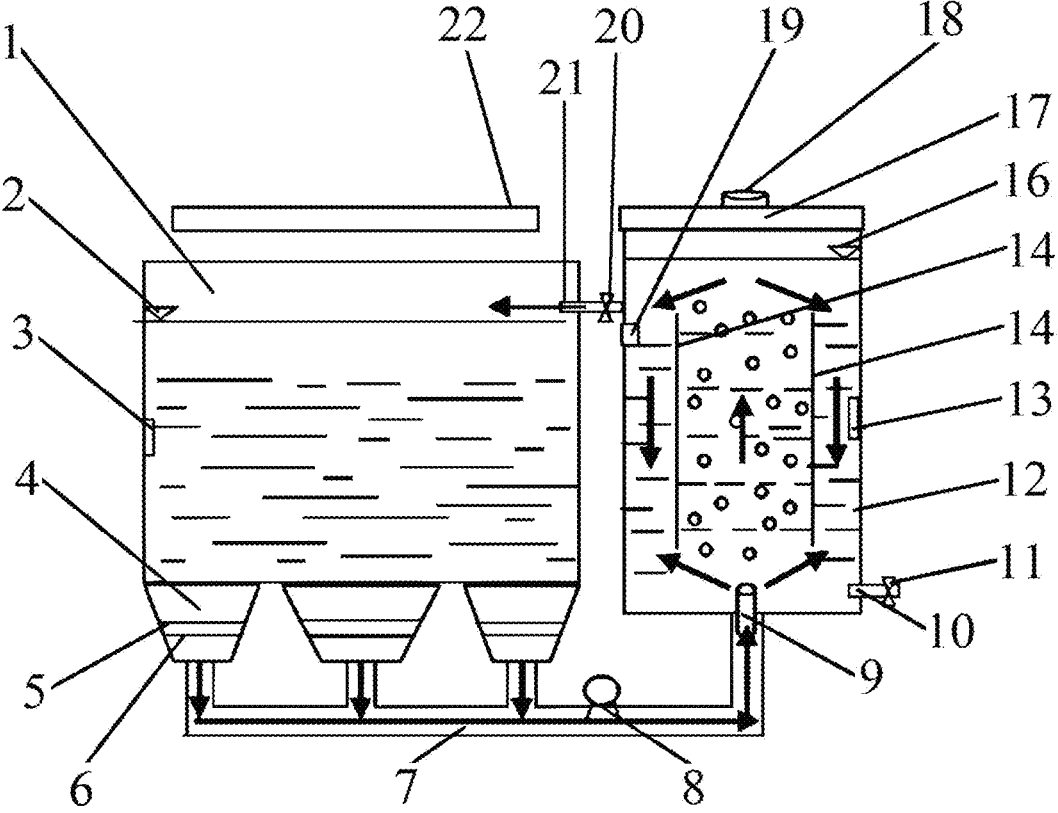
FIG. 1 is a schematic structural diagram according to the disclosure.
Figure 2:
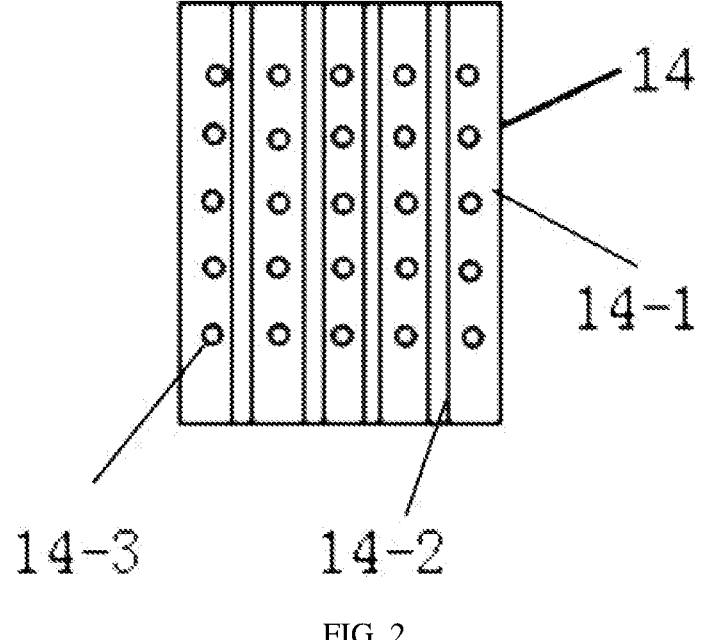
FIG. 2 is a front view of a guide plate according to the disclosure.
Figure 3:
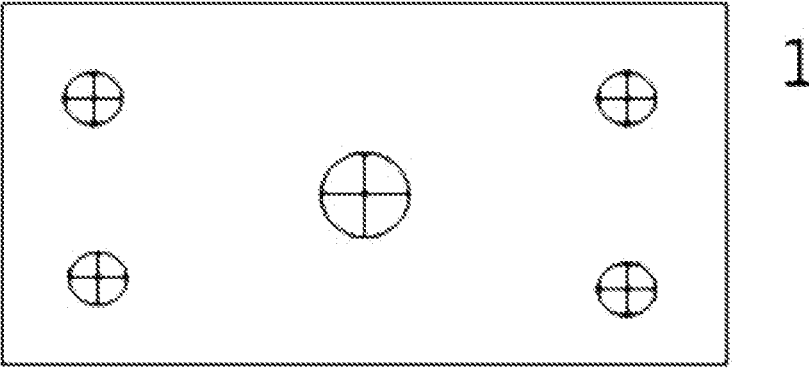
FIG. 3 is a top view of a first shell according to the disclosure.
Figure 5:
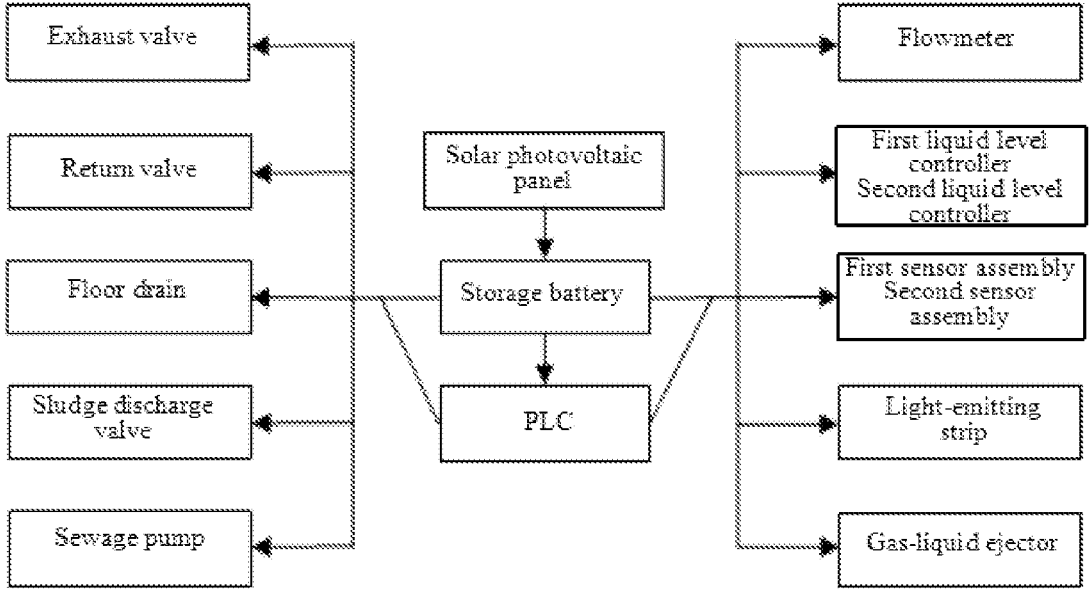
FIG. 5 is a schematic diagram of connection of functional devices according to the disclosure.

With reference to FIGS. 1-5, this embodiment provides a device for cooperatively treating aquaculture tail water by algae and bacteria, including an aquaculture part, where a bottom of the aquaculture part is communicated with one end of a sewage discharge part, and an other end of the sewage discharge part is communicated with a bottom of a tail water treatment part, and an upper side wall of the tail water treatment part is communicated with an upper side wall of the aquaculture part.

The sewage discharge part includes a sewage pipe 7 communicated with the bottom of the aquaculture part, one end of the sewage pipe 7 away from the aquaculture part is communicated with the bottom of the tail water treatment part, and a sewage pump 8 is arranged on the sewage pipe 7.

The tail water treatment part includes a second shell 12, where a bottom end of the second shell 12 is communicated with the sewage pipe 7, and a top end of a side wall of the second shell 12 is communicated with an upper part of the side wall of the aquaculture part. Several guide plates 14 are arranged in the second shell 12, and microalgae are inoculated on outer side walls of the guide plates 14.

In the disclosure, aquaculture organisms are cultured in the aquaculture part. The aquaculture tail water in the aquaculture part is sent into the second shell 12 by the sewage pump 8 through the sewage pipe 7, and the guide plates 14 in the second shell 12 are inoculated with the microalgae. The microalgae and original microorganisms in the aquaculture tail water form a algae-bacteria symbiont. Therefore, the aquaculture tail water is treated, and then, the treated water is introduced into the aquaculture part again.

In a further optimization scheme, the aquaculture part includes a first shell 1, where a first liquid level controller 2 is arranged in the first shell 1, a first sensor assembly 3 is fixedly installed on an inner side wall of the first shell 1, and a bottom end of the first shell 1 is communicated with at least one sewage collection tank 4, and a bottom end of the sewage collection tank 4 is communicated with the sewage pipe 7. A water level in the first shell 1 is controlled by the first liquid level controller 2, and water data in the first shell 1 (including but not limited to water temperature, dissolved oxygen in the water, water turbidity and ammonia nitrogen content in the water) is monitored by the first sensor assembly 3, and the data is transmitted to a programmable logic controller (PLC controller). When the water data in the first shell 1 reaches a set value, the PLC controller controls the sewage pump 8 to start, and the aquaculture tail water is pumped into the second shell 12 for treatment. A solar photovoltaic panel 22 is also arranged above the first shell 1, solar energy is converted into electric energy by the solar photovoltaic panel 22 and stored in a storage battery to provide all or part of the electric energy for the device. The bottom end of the first shell 1 is preferably rectangular, and floor drains are arranged at four corners of the bottom end and a middle part of the bottom end of the first shell 1. Fan blades are rotatably connected in the floor drains, and the fan blades are connected with a motor which is electrically connected with the PLC controller. The fan blades are used for feeding the aquaculture tail water in the first shell 1 into the sewage collection tank 4. The aquaculture tail water in different positions flows to the sewage collection tank 4 uniformly through the floor drains, and then enters the second shell 12 for the treatment, so a circulation effect of the aquaculture tail water is ensured. A preferred model of the first liquid level controller 2 is ZX/CYH0-LTC1000-5-3-L.

In a further optimization scheme, an ecological bed substrate layer 5 and an escape prevention net 6 are sequentially arranged in the sewage collection tank 4 from top to bottom. The escape prevention net 6 is fixedly connected to an inner side wall of the sewage collection tank 4 and horizontally arranged, and the ecological bed substrate layer 5 is placed above the escape prevention net 6. The ecological bed substrate layer 5 is a loose structure, so as not to block the escape prevention net 6. Meanwhile, the ecological bed substrate layer 5 not passes through the escape prevention net 6. The ecological bed substrate layer 5 is preferably consists of natural zeolites or gravels, and is used for preliminarily treating ammonia nitrogen, total nitrogen and total phosphorus in the aquaculture tail water, helping to prevent a nitration reaction in the second shell 12 and prevent nitrite accumulation in the second shell 12, so as not to affect stability of a circulation system. The escape prevention net 6 may prevent aquatic animals from being sucked into the second shell 12, and may also filter large-volume impurities.

In a further optimization scheme, the several guide plates 14 are fixedly connected to an inner side wall of the second shell 12. The several guide plates 14 are arranged in parallel with each other, and the guide plates 14 are arranged vertically, and side walls of the guide plates 14 are not in contact with the inner side wall of the second shell 12. The several guide plates 14 are arranged in parallel. When water flows between the guide plates 14 to a top end of the second shell 12 under an action of the sewage pump 8, the water flows to a bottom end of the second shell 12 through gaps between the guide plates 14 and the inner side walls of the second shell 12, thereby increasing a treatment speed of the tail water.

In a further optimization scheme, a plurality of light-emitting strips 14-2 are fixedly connected to the outer side walls of the guide plates 14. The plurality of light-emitting strips 14-2 are sequentially arranged at intervals, and the light-emitting strips 14-2 are vertically arranged. A plurality of holes 14-3 are arranged between each two adjacent light-emitting strips 14-2, and the holes 14-3 are arranged on each of the guide plates 14 and penetrate through each of the guide plates 14, and the plurality of holes 14-3 are sequentially arranged at intervals from top to bottom. Several membranes 14-1 are laid on the outer wall of each of the guide plates 14, and each of the membranes 14-1 is located between each two adjacent light-emitting strips 14-2. The membranes 14-1 do not cover the holes 14-3.

Materials of the membranes 14-1 may be polyvinylidene fluoride (PVDF) membranes or non-woven biofilms, and materials of the guide plates 14 are preferably polyvinyl chloride (PVC) plates, stainless steel plates or glass plates. The holes 14-3 may improve a fluidity of an algae-bacteria symbiotic system, and the light-emitting strips 14-2 provide lighting conditions for normal physiological activities of the algae-bacteria symbiotic system, thus ensuring a water purification effect.

In a further optimization scheme, a second liquid level controller 16 is arranged in the second shell 12, a second sensor assembly 13 is fixedly installed on the inner side wall of the second shell 12, a flowmeter 19 is fixedly installed on the inner side wall of the second shell 12, and a return pipe 21 is fixedly connected and communicated with the side wall of the second shell 12. The return pipe 21 is positioned at a top end of the second shell 12, and one end of the return pipe 21 away from the second shell 12 extends into the first shell 1. The return pipe 21 is provided with a return valve 20, one end of the return pipe 21 extending into the first shell 1 is located above the first liquid level controller 2, an other end of the return pipe 21 is located below the second liquid level controller 16, and the flowmeter 19 is close to the other end of the return pipe 21. The second sensor assembly 13 is used to monitor water data in the second shell 12, the second liquid level controller 16 is used to control a water level in the second shell 12, and the flowmeter 19 is used to monitor a water flow into the first shell 1. One end of return pipe 21 extending into the first shell 1 is located above the first liquid level controller 2, that is, one end of the return pipe 21 extending into the first shell 1 is located above a water surface. The other end of return pipe 21 is located below the second liquid level controller 16, that is, the other end of return pipe 21 extends into the second shell 12 and is below the water level. Thus, there is a difference between the water level in the second shell 12 and the water level in the first shell 1, and the treated tail water may smoothly flow from the second shell 12 to the first shell 1, which is conducive to stability of a circulation treatment process of the aquaculture tail water, and energy consumption of a water pump is also reduced. A preferred model of the second liquid level controller 16 is ZX/CYH0-LTC1000-5-3-L.

In a further optimization scheme, an outer side wall of the second shell 12 is fixedly connected with and communicated with a sludge discharge pipe 10. The sludge discharge pipe 10 is located at the bottom end of the second shell 12, and the sludge discharge pipe 10 is provided with a sludge discharge valve 11. Sludge deposited in the second shell 12 is discharged out of the second shell 12 through the sludge discharge pipe 10.

In a further optimization scheme, the top end of the second shell 12 is detachably connected with a top screw cover 17, and the top screw cover 17 is fixedly connected with and communicated with an exhaust valve 18. With this arrangement, it is convenient for liquid adding, exhausting and cleaning of the second shell 12.

In a further optimization scheme, a gas-liquid ejector 9 is arranged below the second shell 12, and the gas-liquid ejector 9 is communicated with the sewage pipe 7 and located between the sewage pump 8 and the second shell 12. Before the aquaculture tail water is introduced into the second shell 12, the aquaculture tail water first passes through the gas-liquid ejector 9. The gas-liquid ejector 9 introduces air into the sewage pipe 7, so that the air and the aquaculture tail water are violently mixed. Meanwhile, liquid may be replenished into the second shell 12 through the gas-liquid ejector 9.

As shown in FIG. 6, a method for cooperatively treating aquaculture tail water by algae and bacteria includes following steps:

S1, determining aquaculture species, placing the aquaculture species in an aquaculture device for breeding, and constructing an aquaculture area;

S2, determining species of water purifying algae, and placing the water purifying algae into a tail water treatment device, and constructing a tail water treatment area;

S3, introducing the aquaculture tail water into the second shell 12 through the sewage pipe 7, and treating the aquaculture tail water by the microalgae on the guide plates 14 in cooperation with the microorganisms in the aquaculture tail water; and S4, returning treated purified water to the aquaculture device.

Specific steps are as follows.

The aquaculture species are determined and placed in the aquaculture device for the breeding, and the aquaculture area is constructed.

The species of the water purifying algae are determined and are put into the tail water treatment device, and the tail water treatment area is constructed.

The aquaculture tail water is filtered through the sewage collection tank at a bottom of the aquaculture area and then discharged into the sewage discharge device.

The filtered aquaculture tail water is discharged to the gas-liquid ejector through the sewage discharge device.

The aquaculture tail water is intensively mixed with air in the gas-liquid ejector and then discharged to the tail water treatment area.

The aquaculture tail water mixed with the air flows upwards into centers of a first guide plate and a second guide plate by using the gas-liquid ejector, and then flows downwards from outer sides of the first guide plate and the second guide plate to form a circular flow for the treatment of the aquaculture tail water.

The treated aquaculture tail water is regularly discharged into the aquaculture device through the water return device.

In this device, the first liquid level controller 2, the first sensor assembly 3, the sewage pump 8, the gas-liquid ejector 9, the sludge discharge valve 11, the second sensor assembly 13, the second liquid level controller 16, the exhaust valve 18, the flowmeter 19, the return valve 20 and the light-emitting strips 14-2 are all electrically connected with the PLC controller. The first liquid level controller 2, the first sensor assembly 3, the sewage pump 8, the gas-liquid ejector 9, the sludge discharge valve 11, the second sensor assembly 13, the second liquid level controller 16, the exhaust valve 18, the flowmeter 19, the return valve 20, and light-emitting strips 14-2 are all electrically connected to the storage battery.

According to the device, newly inoculated microalgae and the original microorganisms in the aquaculture tail water form an algae-bacteria symbiosis by coupling a membrane photobioreactor and an airlift reactor and taking the membranes as carriers. The device has advantages of simultaneous carbon and nitrogen reduction and phosphorus removal, low impact on the aquaculture organisms, and significant improvement in an effluent quality without subsequent sedimentation devices. Fluidity and stability of an algae-bacteria reaction solution are also improved by using new guide plates, and a circulating flow of water quality is promoted by adding sewage suction sites, thus realizing quality improvement and efficiency improvement of the treatment of the aquaculture tail water.

A co-culture of fish, algae and bacteria is realized by coupling aquaculture and microalgae culture and recycling the aquaculture tail water. Not only are there catches, the microalgae may also be recycled and utilized, adding an economic benefit and achieving resource utilization of the sewage.

Effluent through a head difference is not only beneficial to stability of a diversion process, but also reduces energy consumption of the water pump. Erecting the solar photovoltaic panel above the aquaculture area not only provides shade for an aquaculture system, but also saves energy, realizing a "fishery-solar hybrid project". The solar energy completely or partially replaces conventional electric energy, saving energy and protecting environment.

This scheme greatly improves an automation degree of the existing system, saves manpower and material resources, and is beneficial to large-scale application.

An Experimental Example of the Disclosure

Aquaculture animals that may be selected by this device include fish, shellfish, shrimps and crabs, etc. The solar photovoltaic panel 22 may be started in advance, and kept in a working state for a long time. According to known parameters, normal working parameter ranges of the first liquid level controller 2 and the first sensor assembly 3 are preset, and aquaculture species and feeds are put in.

The species of the water purifying algae are determined and expanded cultured, purified and domesticated in advance. Optional algae species include *Haematococcus pluvialis*, Scenedesmus filamentous, *Chlorella vulgaris* and *Spirulina platensis*. Working cycles of the light-emitting strips 14-2, the gas-liquid ejector 9 and the return valve 20 are set.

The second liquid level controller 16 is arranged to ensure that a liquid surface in the second shell 12 is always higher than the return valve 20, so that after the return valve 20 is opened, the liquid in the aquaculture tail water treatment area may be automatically discharged under an action of a water level difference, and the algae-bacteria reaction solution may flow evenly and the reaction system is more stable.

The top screw cover 17 is opened to inoculate the expanded cultured, purified and domesticated algae species into the aquaculture tail water treatment area according to a predetermined inoculation concentration, and then the top screw cover 17 is closed. Preferably, an inoculation concentration of *Spirulina platensis* is at least 0.12 g/L.

The floor drains, the sewage pump 8 and the gas-liquid ejector 9 are started in turn.

The aquaculture tail water flows through the floor drains in turn, is preliminarily purified on the ecological bed substrate layer 5 of the sewage collection tank 4, and then, is filtered through the escape prevention net 6, passes through the sewage pipe 7 to the sewage pump 8. The sewage pump 8 may physically decompose fibrous dirt, silt and solid particles with a set range of particle size. Then, the aquaculture tail water passes through the sewage pipe 7 to the gas-liquid ejector 9, so that the aquaculture tail water is violently mixed with the air sucked by an internal structure of the gas-liquid ejector 9, and a gas-liquid mixture is discharged upward along the gas-liquid ejector 9. After passing through the several guide plates 14, the aquaculture tail water flows downward along the gaps between the guide plates 14 and the inner side walls of the second shell 12 to form a circular flow.

The return valve 20 is opened according to a set time, and the liquid in the aquaculture tail water treatment area flows to the first shell 1 through the return pipe 21, and the return valve 20 is closed according to the set time.

The sludge discharge valve 11 is opened according to the set time to collect microalgae sludge.

According to a device and a method for cooperatively treating aquaculture tail water by algae and bacteria, at beginning of the reaction in the aquaculture tail water treatment area, the light-emitting strips 14-2 may be set for continuous lighting, and meanwhile the gas-liquid ejector 9 is set for continuous aeration, so as to rapidly circulate culture medium components. Then, the floor drains and the sewage pump 8 are turned on. At this time, working times and working cycles of the gas-liquid ejector 9 and the light-emitting strips 14-2 may be changed according to characteristics of water purification by the microalgae, so as to save energy while ensuring a coordinated growth of algae and bacteria and water purification.

Oxygen released by algae through photosynthesis is supplied to aerobic heterotrophic microorganisms for metabolic activities, while oxidative decomposition of organic pollutants is carried out by aerobic microorganisms, and metabolic products of carbon dioxide, inorganic nitrogen and phosphorus compounds are supplied to the algae as carbon sources and nutrients required by the photosynthesis. When the flowmeter 19 shows that the effluent is stable, working cycles of the return valve 20 and the sludge discharge valve 11 are set again. In addition, it is necessary to set an exhaust valve 18 to vent regularly to prevent nitrite accumulation in the aquaculture tail water treatment area.

By applying the disclosure, an automatic cycling treatment of the aquaculture tail water may be realized only by setting relevant parameters of the aquaculture area and an aquaculture tail water purification area in advance. After an application of the disclosure, indexes such as total nitrogen, total phosphorus and ammonia nitrogen in the aquaculture tail water are obviously reduced, a eutrophication degree is improved, and the water quality meets requirements of recirculating aquaculture or reaches a discharge standard.

In a description of the disclosure, it should be understood that terms "vertical", "horizontal", "up", "down", "front", "back", "left", "right", "vertical", "horizontal", "top", "bottom", "inside", "outside", and other indications of orientation or positional relationships are based on orientation or positional relationships shown in the accompanying drawings, solely for a convenience of describing the disclosure, rather than indicating or implying that a device or a component referred to must have a specific orientation, be constructed and operated in a specific orientation, therefore it may not be understood as a limitation of the disclosure.

The above-mentioned embodiments only describe a preferred mode of the disclosure, and do not limit the scope of the disclosure. Under a premise of not departing from a design spirit of the disclosure, various modifications and improvements made by ordinary technicians in the field to the technical scheme of the disclosure shall fall within the scope of protection determined by claims of the disclosure.

What is claimed is:

1. A device for cooperatively treating aquaculture tail water by algae and bacteria, comprising: an aquaculture part, wherein a bottom of the aquaculture part is communicated with one end of a sewage discharge part, and an other end of the sewage discharge part is communicated with a bottom of a tail water treatment part, and an upper side wall of the tail water treatment part is communicated with an upper side wall of the aquaculture part;

wherein the sewage discharge part comprises a sewage pipe communicated with the bottom of the aquaculture part, one end of the sewage pipe away from the aquaculture part is communicated with the bottom of the tail water treatment part, and a sewage pump is arranged on the sewage pipe;

the aquaculture part comprises a first shell, a first liquid level controller is arranged in the first shell, a first sensor assembly is fixedly installed on an inner side wall of the first shell, a bottom end of the first shell is communicated with at least one sewage collection tank, and a bottom end of the at least one sewage collection tank is communicated with the sewage pipe; and the tail water treatment part comprises a second shell, wherein a bottom end of the second shell is communicated with the sewage pipe, and a top end of a side wall of the second shell is communicated with the upper side wall of the aquaculture part; a plurality of guide plates are arranged in the second shell, and microalgae are inoculated on an outer side wall of each of the plurality of guide plates.

2. The device for cooperatively treating the aquaculture tail water by the algae and the bacteria according to claim 1, wherein an ecological bed substrate layer and an escape prevention net are sequentially arranged in the at least one sewage collection tank from top to bottom; the escape prevention net is fixedly connected to an inner side wall of the at least one sewage collection tank and horizontally arranged, and the ecological bed substrate layer is placed above the escape prevention net.

3. The device for cooperatively treating the aquaculture tail water by the algae and the bacteria according to claim 1, wherein the plurality of guide plates are fixedly connected to an inner side wall of the second shell; the plurality of guide plates are arranged in parallel with each other, and the plurality of guide plates are arranged vertically, and side walls of the plurality of guide plates are not in contact with the inner side wall of the second shell.

4. The device for cooperatively treating the aquaculture tail water by the algae and the bacteria according to claim 1, wherein a plurality of light-emitting strips are fixedly connected to the outer side wall of each of the plurality of guide plates; the plurality of light-emitting strips are sequentially arranged at intervals, and the plurality of light-emitting strips are vertically arranged; a plurality of holes are arranged between each two adjacent light-emitting strips of the plurality of light-emitting strips, and the plurality of holes are arranged on each of the plurality of guide plates and penetrate through each of the plurality of guide plates, and the plurality of holes are sequentially arranged at intervals from top to bottom; a plurality of membranes are laid on the outer side wall of each of the plurality of guide plates, and each of the plurality of membranes is located between each two adjacent light-emitting strips of the plurality of light-emitting strips; and the plurality of membranes do not cover the plurality of holes.

5. The device for cooperatively treating the aquaculture tail water by the algae and the bacteria according to claim 1, wherein a second liquid level controller is arranged in the second shell, a second sensor assembly is fixedly installed on an inner side wall of the second shell, a flowmeter is fixedly installed on the inner side wall of the second shell, and a return pipe is fixedly connected and communicated with the side wall of the second shell; the return pipe is positioned at the top end of the side wall of the second shell, and one end of the return pipe away from the second shell extends into the first shell; the return pipe is provided with a return valve, the one end of the return pipe extending into the first shell is located above the first liquid level controller, an other end of the return pipe is located below the second liquid level controller, and the flowmeter is close to the other end of the return pipe.

6. The device for cooperatively treating the aquaculture tail water by the algae and the bacteria according to claim 1, wherein an outer side wall of the second shell is fixedly connected with and communicated with a sludge discharge pipe; the sludge discharge pipe is located at the bottom end of the second shell, and the sludge discharge pipe is provided with a sludge discharge valve.

7. The device for cooperatively treating the aquaculture tail water by the algae and the bacteria according to claim 1, wherein a top end of the second shell is detachably connected with a top screw cover, and the top screw cover is fixedly connected with and communicated with an exhaust valve.

8. The device for cooperatively treating the aquaculture tail water by the algae and the bacteria according to claim 1, wherein a gas-liquid ejector is arranged below the second shell, and the gas-liquid ejector is communicated with the sewage pipe and located between the sewage pump and the second shell.

9. A method for cooperatively treating aquaculture tail water by algae and bacteria, based on the device for cooperatively treating the aquaculture tail water by the algae and the bacteria according to claim 1, comprising following steps:

S1, determining aquaculture species, placing the aquaculture species in the aquaculture part for breeding, and constructing an aquaculture area;

S2, determining species of water purifying algae, and placing the water purifying algae into the tail water treatment part, and constructing a tail water treatment area;

S3, introducing the aquaculture tail water into the second shell through the sewage pipe, and treating the aquaculture tail water by the microalgae on the plurality of guide plates in cooperation with microorganisms in the aquaculture tail water; and S4, returning treated purified water to the aquaculture part.

* * * * *